(12) United States Patent
Solberg et al.

(10) Patent No.: US 6,340,227 B1
(45) Date of Patent: Jan. 22, 2002

(54) EARPLUG SYSTEM

(75) Inventors: Timothy J. Solberg, 1291 Via Constessa, San Marcos, CA (US) 92069; Gary I. Solberg, Staples, MN (US)

(73) Assignee: Timothy J. Solberg, San Marcos, CA (US)

( * ) Notice: Subject to any disclaimer, the term of this patent is extended or adjusted under 35 U.S.C. 154(b) by 0 days.

(21) Appl. No.: 09/805,756

(22) Filed: Mar. 13, 2001

(51) Int. Cl.[7] .................................................. G02C 5/14
(52) U.S. Cl. ........................................ 351/123; 351/158
(58) Field of Search .................................. 351/123, 158

(56) References Cited

U.S. PATENT DOCUMENTS 5,475,449 A * 12/1995 Pyle ........................... 351/123
5,541,677 A * 7/1996 Huhtala ....................... 351/156
5,703,670 A * 12/1997 Callard ....................... 351/123

* cited by examiner

*Primary Examiner*—Huy Mai
(74) *Attorney, Agent, or Firm*—Michael S. Neustel

(57) ABSTRACT

An earplug system for conveniently storing and dispensing earplugs to an individual. The earplug system includes a connector formed for removably connecting to the distal ends of the arms of glasses, a recoil device attached to the connector, a length of cord stored within and dispensed from the recoil device, and an earplug attached to the cord. The recoil device stores the length of cord during non-use of the earplug, however when the user desires to utilize the earplug within their ear they simply draw the cord from the recoil device and insert the earplug into their ear without fear of losing the earplug. In an alternative embodiment of the present invention, the recoil device is permanently positioned within the arms of the glasses for dispensing the length of cord and corresponding earplug.

18 Claims, 10 Drawing Sheets

EARPLUG SYSTEM

BACKGROUND OF THE INVENTION

1. Field of the Invention

The present invention relates generally to earplugs and more specifically it relates to an earplug system for conveniently storing and dispensing earplugs to an individual.

Individuals that work within areas of high noise often times are required to wear earplugs to prevent damage to their hearing. Earplugs reduce the overall level of sounds that enter the ear to avoid ear damage while allowing the individual to still hear the desired sounds. However, conventional earplugs are easily lost or misplaced by individuals resulting in the non-usage of earplugs, which eventually leads to hearing loss. Hence, there is a need for a product that conveniently stores and dispenses earplugs for individuals.

2. Description of the Prior Art

Earplugs have been in use for years. Earplugs are typically constructed of a resilient foam material with a tapered structure and rounded tip. Earplugs may include a cord to connect a pair of earplugs to allow continued reuse of the earplugs. Earplugs are typically constructed of a disposable design, however permanent earplugs are available for continued usage. There are various other designs and structures of earplugs as can be desired by one skilled in the art. BILSOM is a manufacture of disposable foam earplugs that are representative of the prior art.

The main problem with conventional earplugs is that they are easily lost or misplaced during everyday activities which results in individuals not utilizing the earplugs as may be required. Since individuals are unable to properly utilize the earplugs they risk losing a portion of their hearing extended periods of time. Another problem with conventional earplugs is that they are not convenient to utilize often times requiring individuals to store the earplugs in awkward containers or unprotected within their pockets.

Examples of patented earplug devices which are illustrative of such prior art include U.S. Pat. 6,074,060 to Bruce; U.S. Pat. 6,067,664 to Cortes; U.S. Pat. 5,475,449 to Pyle; U.S. Pat. 5,541,677 to Huhtala; U.S. Pat. 5,781,272 to Bright et al.; U.S. Pat. 5,703,670 to Callard; U.S. Pat. 3,943,925 to Leight.

While these devices may be suitable for the particular purpose to which they address, they are not as suitable for conveniently storing and dispensing earplugs to an individual. Conventional earplug devices are not suitable for usage in everyday situations.

In these respects, the earplug system according to the present invention substantially departs from the conventional concepts and designs of the prior art, and in so doing provides an apparatus primarily developed for the purpose of conveniently storing and dispensing earplugs to an individual.

SUMMARY OF THE INVENTION

In view of the foregoing disadvantages inherent in the known types of earplugs now present in the prior art, the present invention provides new earplug system construction wherein the same can be utilized for conveniently storing and dispensing earplugs to an individual.

The general purpose of the present invention, which will be described subsequently in greater detail, is to provide new earplug system that has many of the advantages of the earplugs mentioned heretofore and many novel features that result in a new earplug system which is not anticipated, rendered obvious, suggested, or even implied by any of the prior art earplugs, either alone or in any combination thereof.

To attain this, the present invention generally comprises a connector formed for removably connecting to the distal ends of the arms of glasses, a recoil device attached to the connector, a length of cord stored within and dispensed from the recoil device, and an earplug attached to the cord. The recoil device stores the length of cord during non-use of the earplug, however when the user desires to utilize the earplug within their ear they simply draw the cord from the recoil device and insert the earplug into their ear without fear of losing the earplug. In an alternative embodiment of the present invention, the recoil device is permanently positioned within the arms of the glasses for dispensing the length of cord and corresponding earplug.

There has thus been outlined, rather broadly, the more important features of the invention in order that the detailed description thereof may be better understood, and in order that the present contribution to the art may be better appreciated. There are additional features of the invention that will be described hereinafter and that will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of the description and should not be regarded as limiting.

A primary object of the present invention is to provide an earplug system that will overcome the shortcomings of the prior art devices.

A second object is to provide earplug system for conveniently storing and dispensing earplugs to an individual.

Another object is to provide earplug system that are removably attachable to various types of glasses including but not limited to prescription glasses, sunglasses, and safety glasses.

An additional object is to provide earplug system that increase the likelihood that workers will wear earplugs.

A further object is to provide earplug system that help reduce the likelihood of hearing damage.

Another object is to provide earplug system that reduces the likelihood of losing earplugs.

Other objects and advantages of the present invention will become obvious to the reader and it is intended that these objects and advantages are within the scope of the present invention.

To the accomplishment of the above and related objects, this invention may be embodied in the form illustrated in the accompanying drawings, attention being called to the fact, however, that the drawings are illustrative only, and that changes may be made in the specific construction illustrated and described within the scope of the appended claims.

BRIEF DESCRIPTION OF THE DRAWINGS

Various other objects, features and attendant advantages of the present invention will become fully appreciated as the same becomes better understood when considered in conjunction with the accompanying drawings, in which like reference characters designate the same or similar parts throughout the several views, and wherein.

DESCRIPTION OF THE PREFERRED EMBODIMENT

Figure 1:
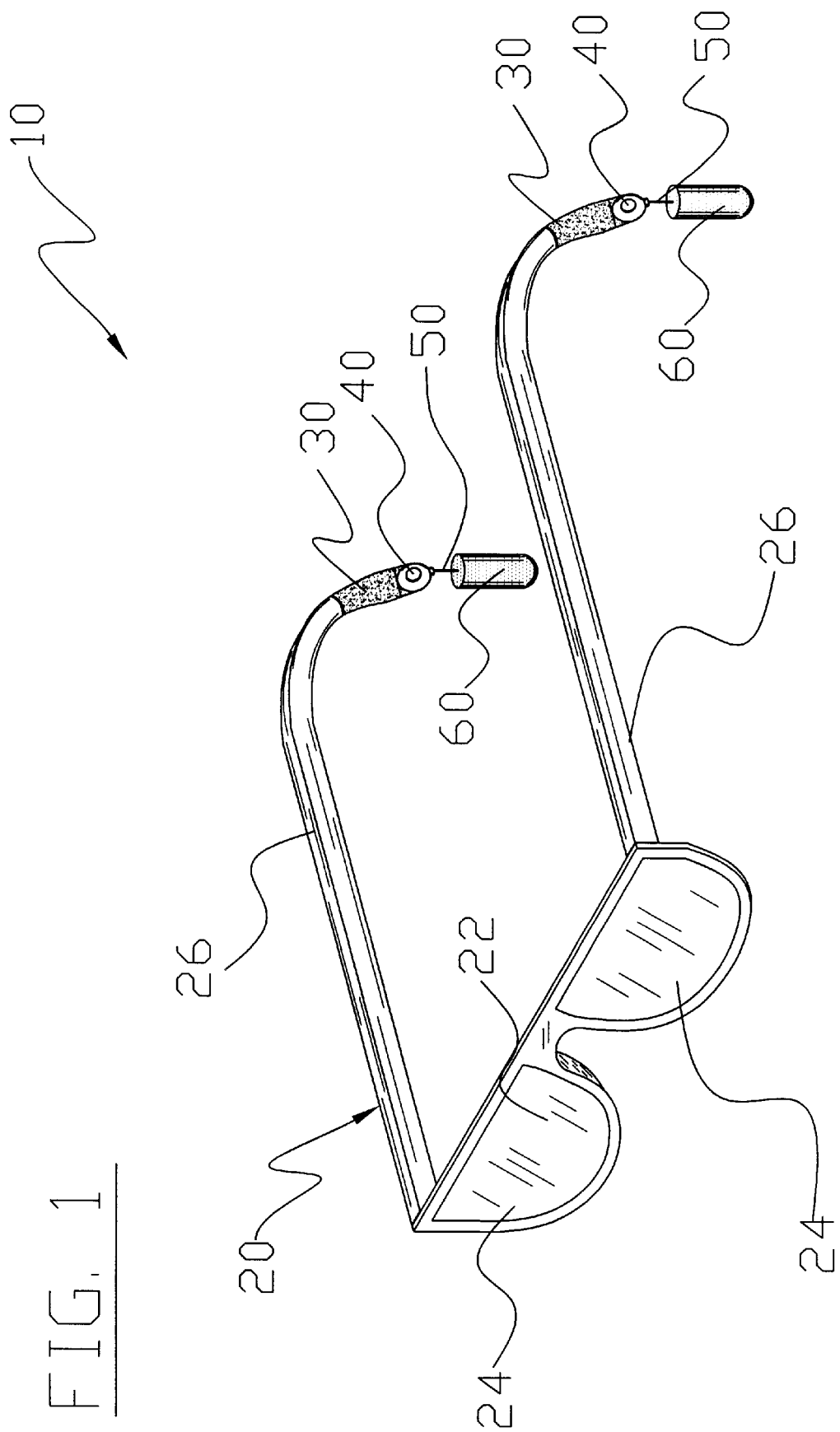
FIG. 1 is an upper perspective view of the present invention attached to the arms of a pair of glasses with the earplugs retracted.

Turning now descriptively to the drawings, in which similar reference characters denote similar elements throughout the several views, FIGS. 1 through 10 illustrate an earplug system 10, which comprises a connector 30 formed for removably connecting to the distal ends of the arms 26 of glasses 20, a recoil device 40 attached to the connector 30, a length of cord 50 stored within and dispensed from the recoil device 40, and an earplug 60 attached to the cord 50. The recoil device 40 stores the length of cord 50 during non-use of the earplug 60, however when the user desires to utilize the earplug 60 within their ear they simply draw the cord 50 from the recoil device 40 and insert the earplug 60 into their ear without fear of losing the earplug 60. In an alternative embodiment of the present invention, the recoil device 40 is permanently positioned within the arms 26 of the glasses 20 for dispensing the length of cord 50 and corresponding earplug 60.

Figure 2:
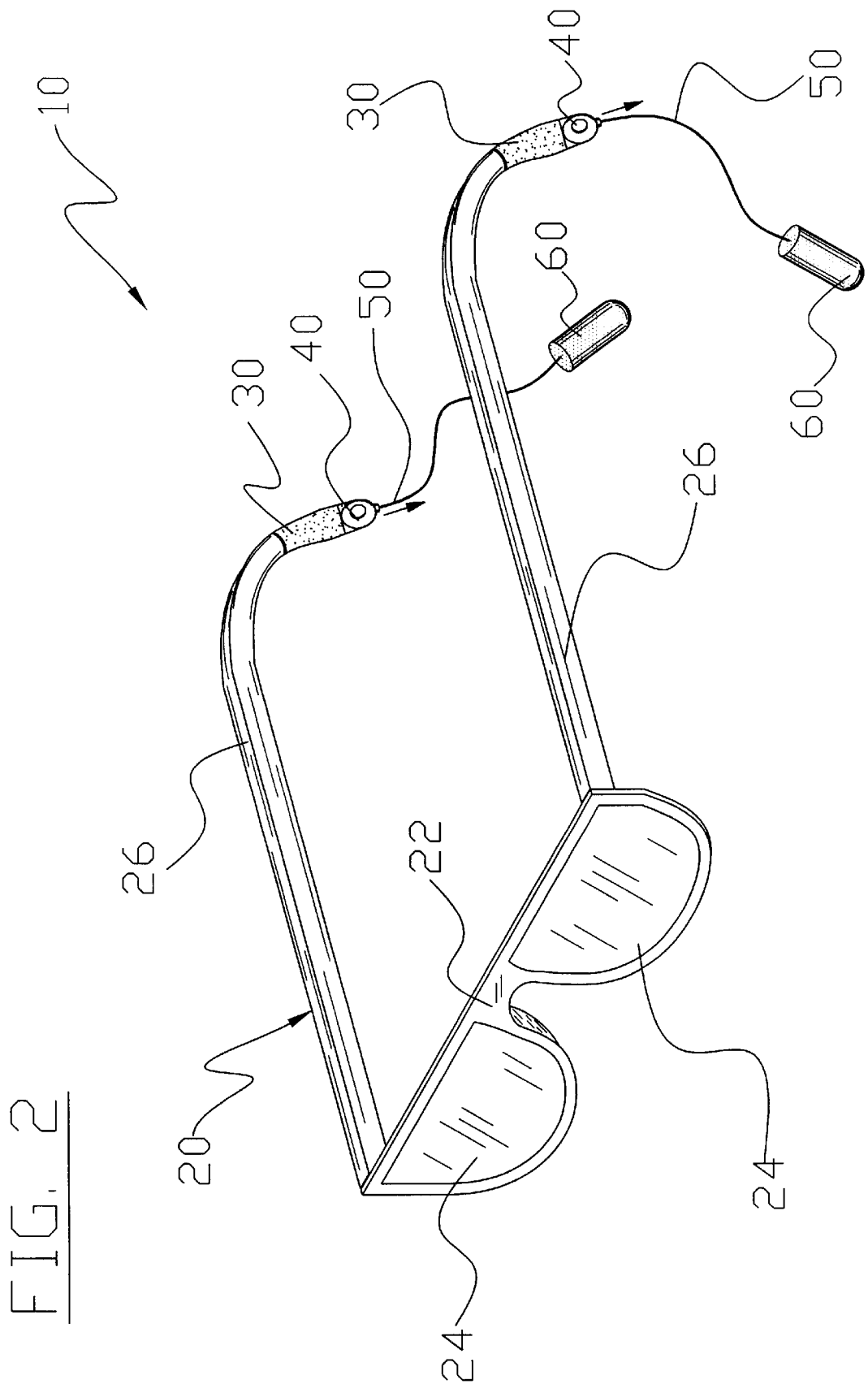
FIG. 2 is an upper perspective view of the present invention attached to the arms of a pair of glasses with the earplugs extended from the recoil device.
Figure 3:
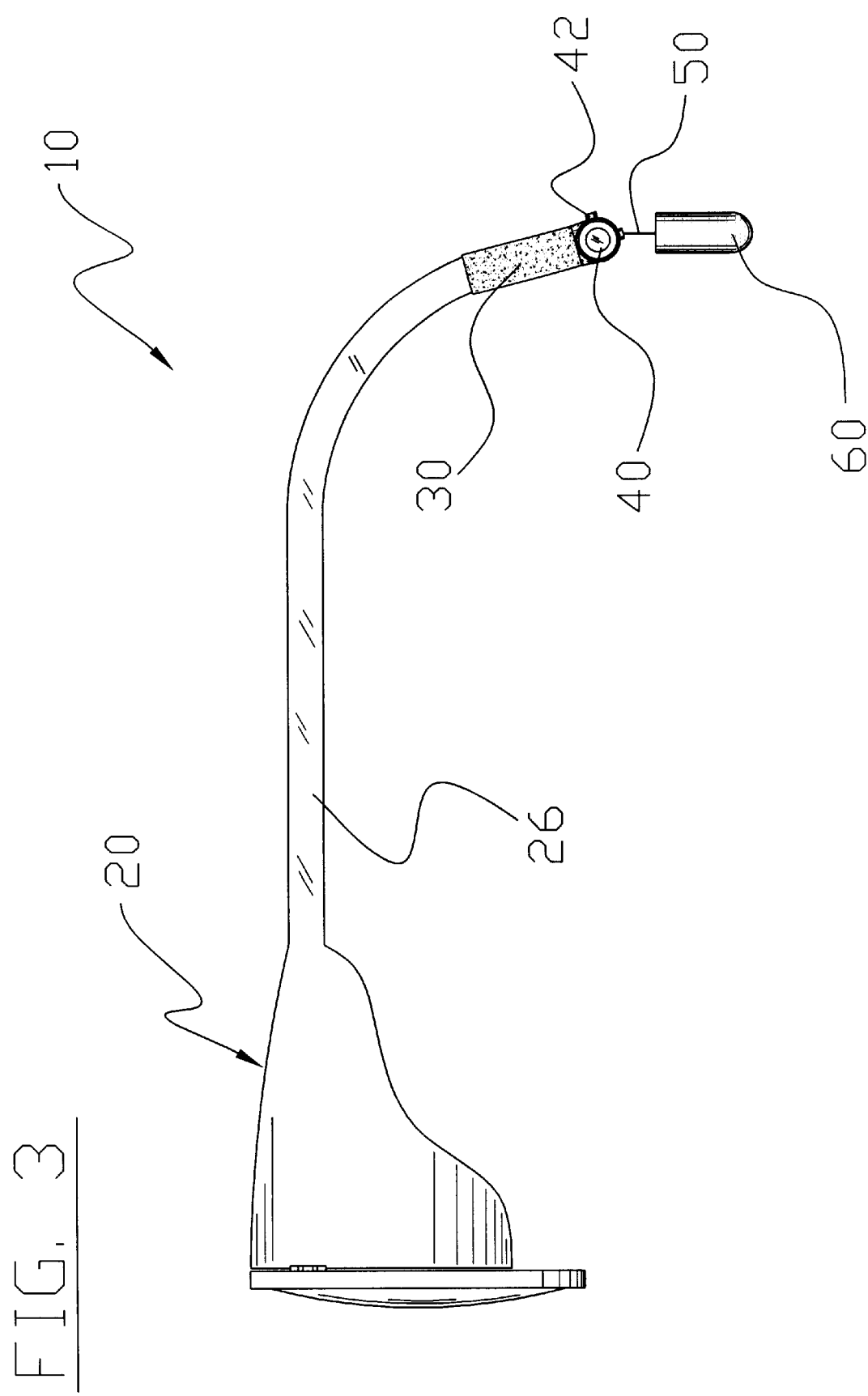
FIG. 3 is a side view of the present invention attached to the arms of a pair of glasses.

As shown in FIGS. 1 through 3 of the drawings, a pair of glasses 20 are generally comprised of a frame 22, a pair of lenses 24 within the frame 22, and a pair of arms 26 attached to the side portions of the frame 22 extending rearwardly. As can be appreciated there are various structures and configurations of glasses 20 available on the market.

Figure 4:
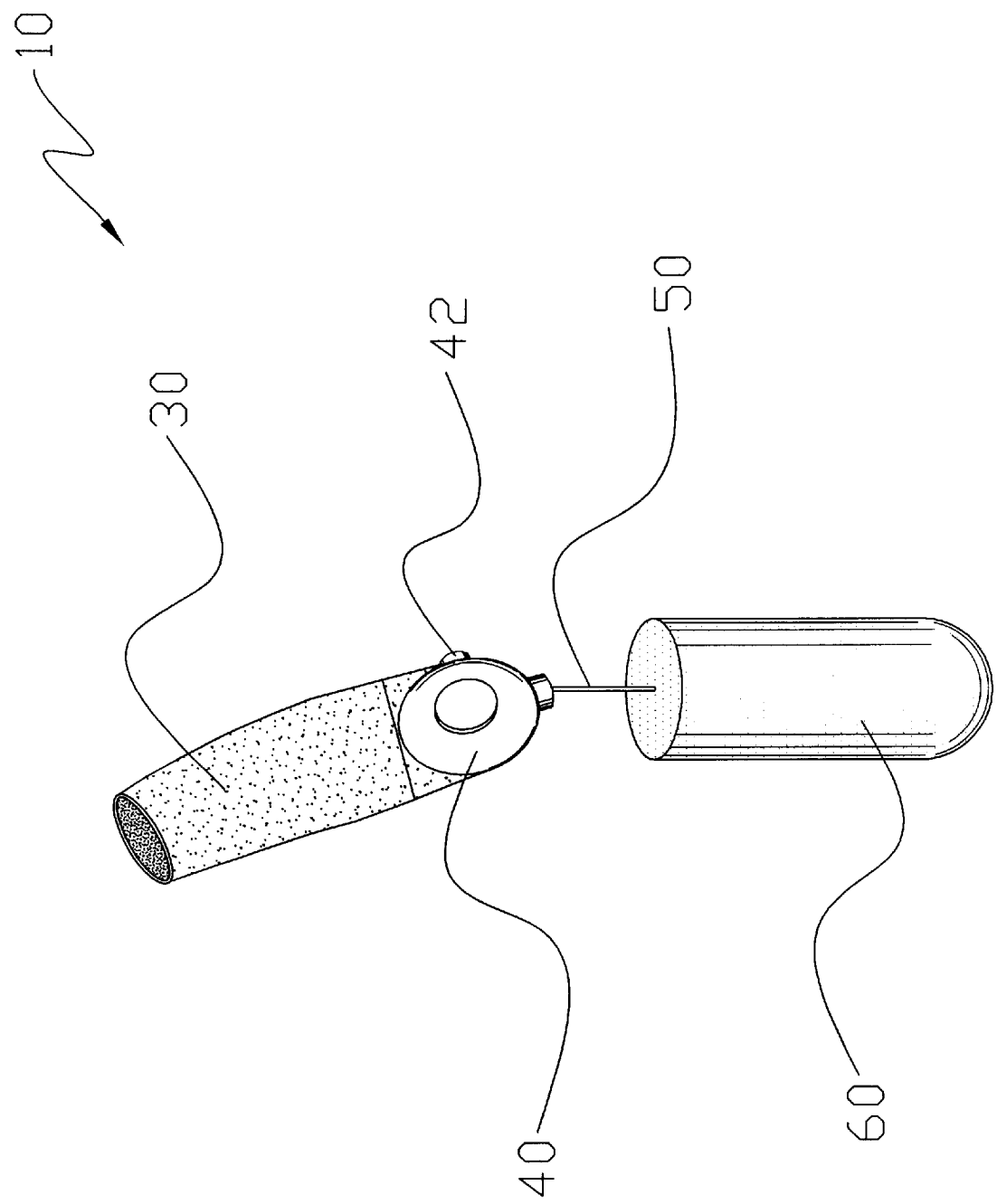
FIG. 4 is an upper perspective view of the present invention.

As best shown in FIG. 4 of the drawings, the connector 30 is a tubular structure having an opening designed to snugly fit about the distal end of the arms 26 of the glasses 20. The connector 30 is preferably constructed of a flexible and resilient material such as but not limited to rubber or plastic. It can be appreciated that the connector 30 may be comprised of a rigid structure that is removably or permanently attached to the arms 26 via conventional attachment means.

Figure 5:
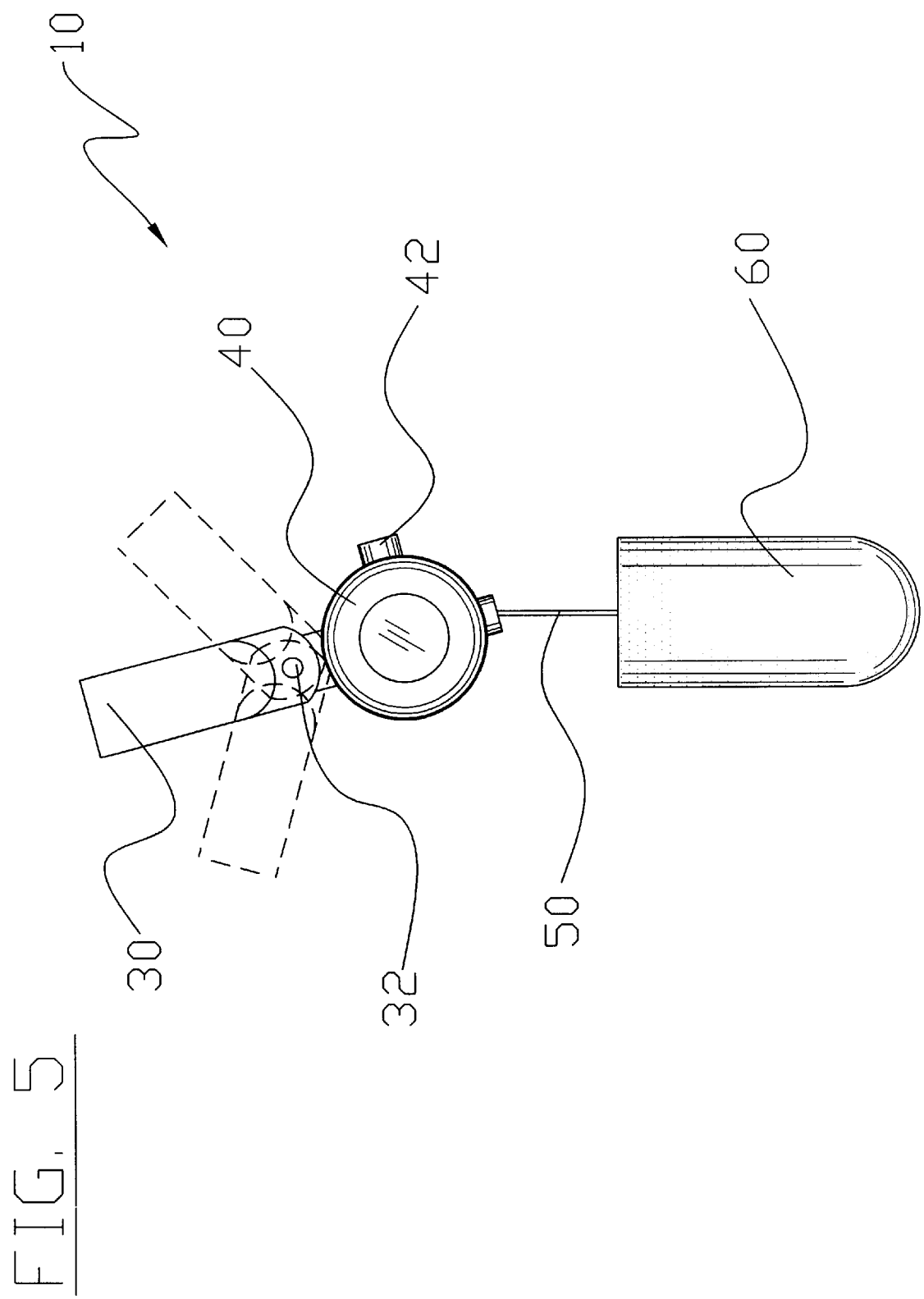
FIG. 5 is a side view of the present invention with a hinge attached between the connector and recoil device.
Figure 6:
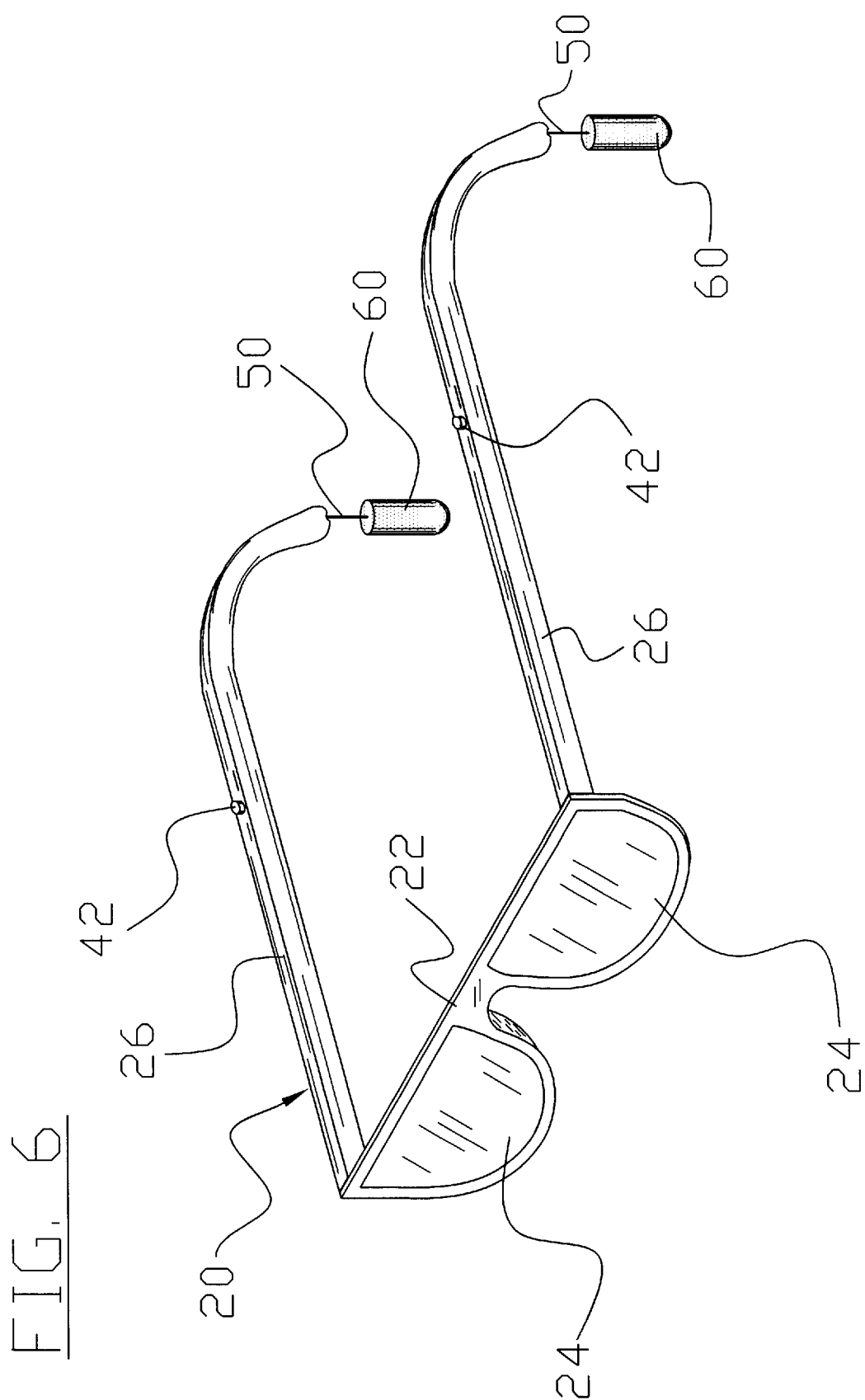
FIG. 6 is an upper perspective view of an alternative embodiment of the present invention.
Figure 7:
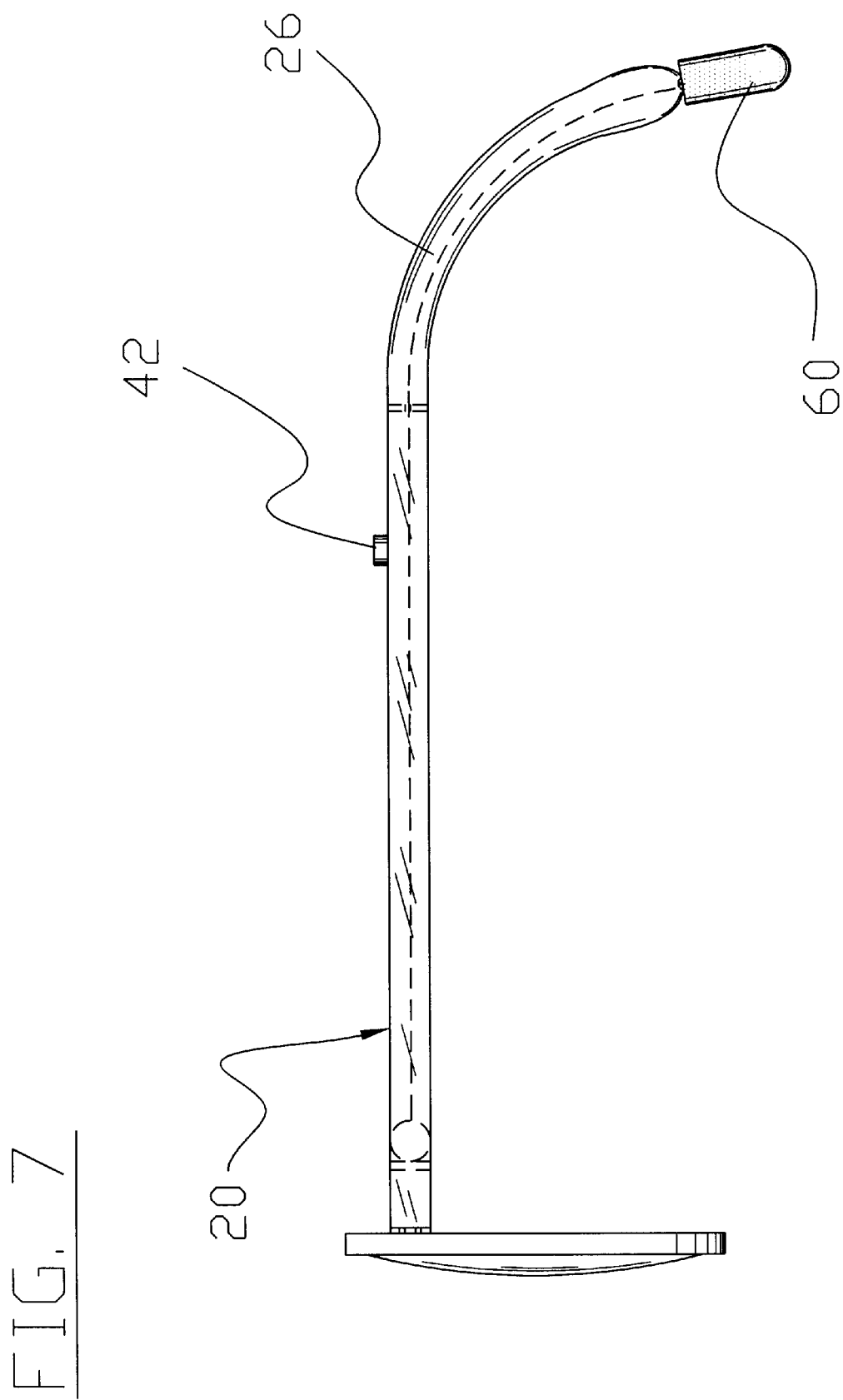
FIG. 7 is a side view of the alternative embodiment.

As further shown in FIGS. 1 through 4 of the drawings, the recoil device 40 is attached to the connector 30 opposite of the opening with the connector 30. The recoil device 40 may also be permanently attached to the arm 26 of the glasses in another embodiment. The recoil device 40 includes a length of cord 50 within that is dispensed from the recoil device 40. The cord 50 is of sufficient length to allow the earplug 60 to be properly positioned within the ear with the cord 50 still retained within the recoil device 40. The recoil device 40 may be comprised of any recoil structure commonly utilized in various industries. A locking button 42 is preferably positioned within the recoil device 40 to allow an individual to selectively lock and release the cord 50 from within the recoil device 40. As shown in FIG. 5 of the drawings, a hinge 32 may be positioned between the connector 30 and the recoil device 40 to allow the recoil device 40 to pivot with respect to the connector 30 and glasses 20.

As shown in FIGS. 1 through 5 of the drawings, the earplug 60 is attached to the end of the cord 50 opposite of the recoil device 40. The earplug 60 is comprised of any well known earplug 60 structure including but not limited to well known foam structures. Various shapes and types of conventional earplug 60 structures may be utilized within the present invention.

Figure 8:
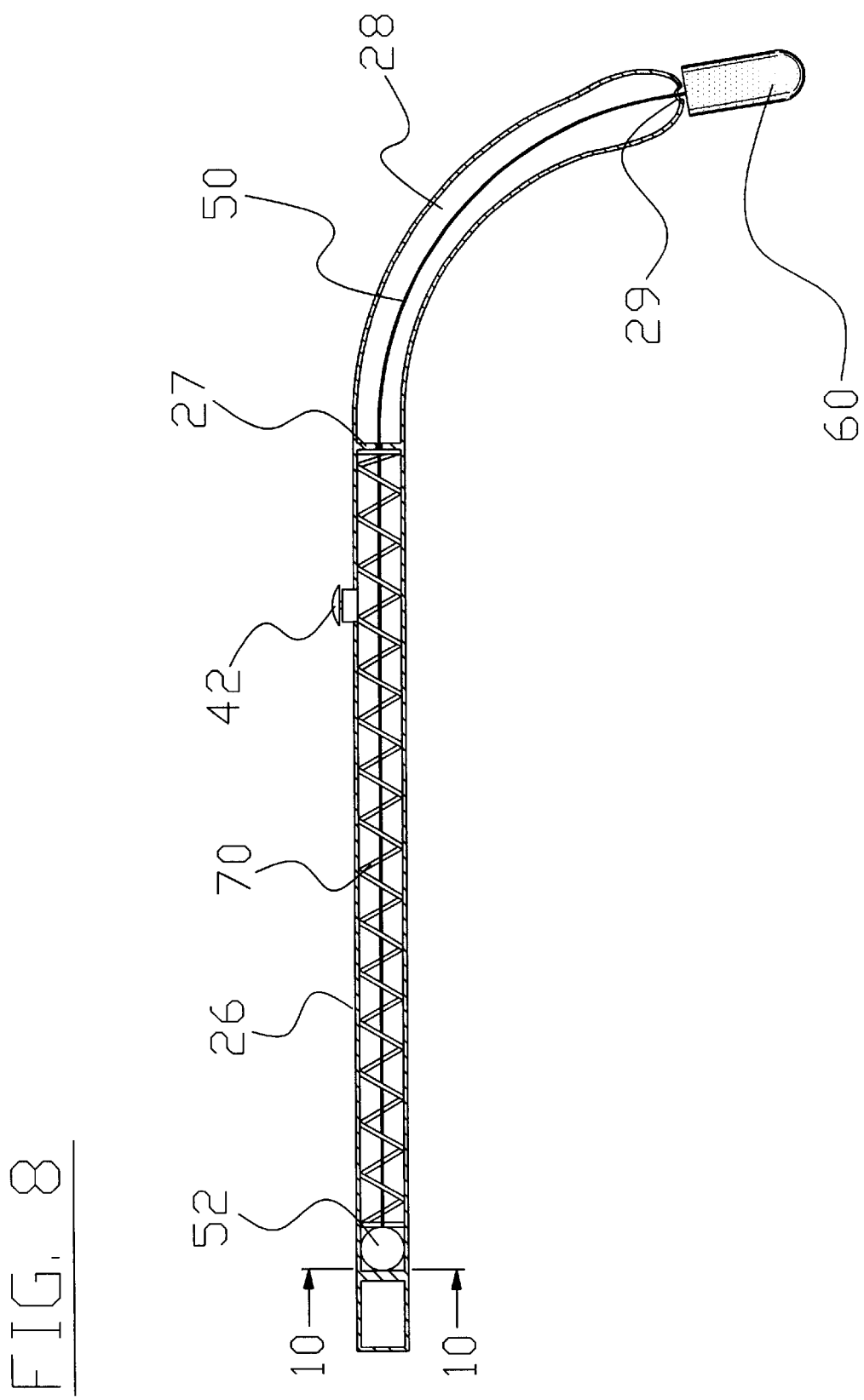
FIG. 8 is a side cutaway view of the alternative embodiment with the earplug retracted into the storage position.
Figure 9:
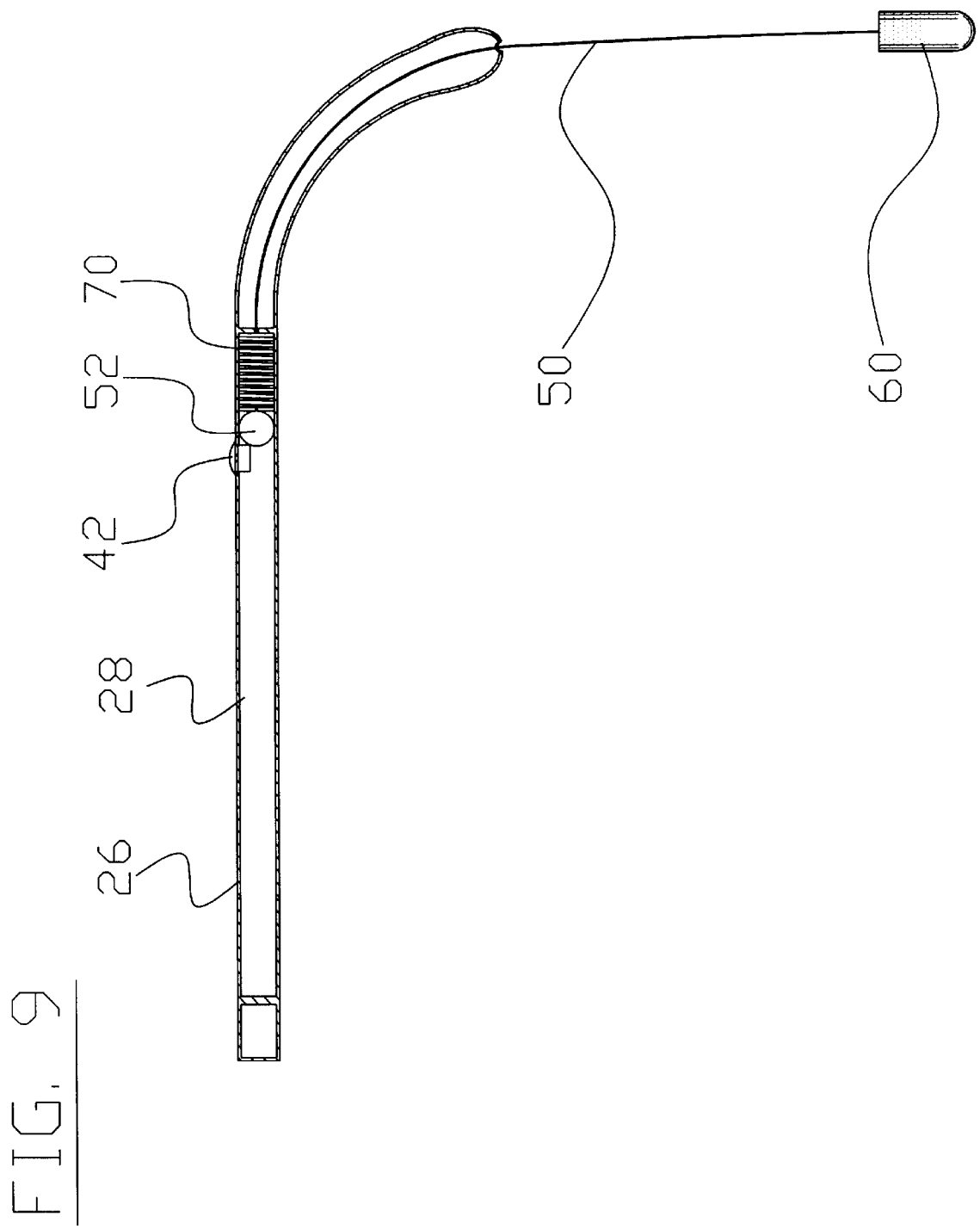
FIG. 9 is a side cutaway view of the alternative embodiment with the earplug extended from the arms of the glasses.
Figure 10:
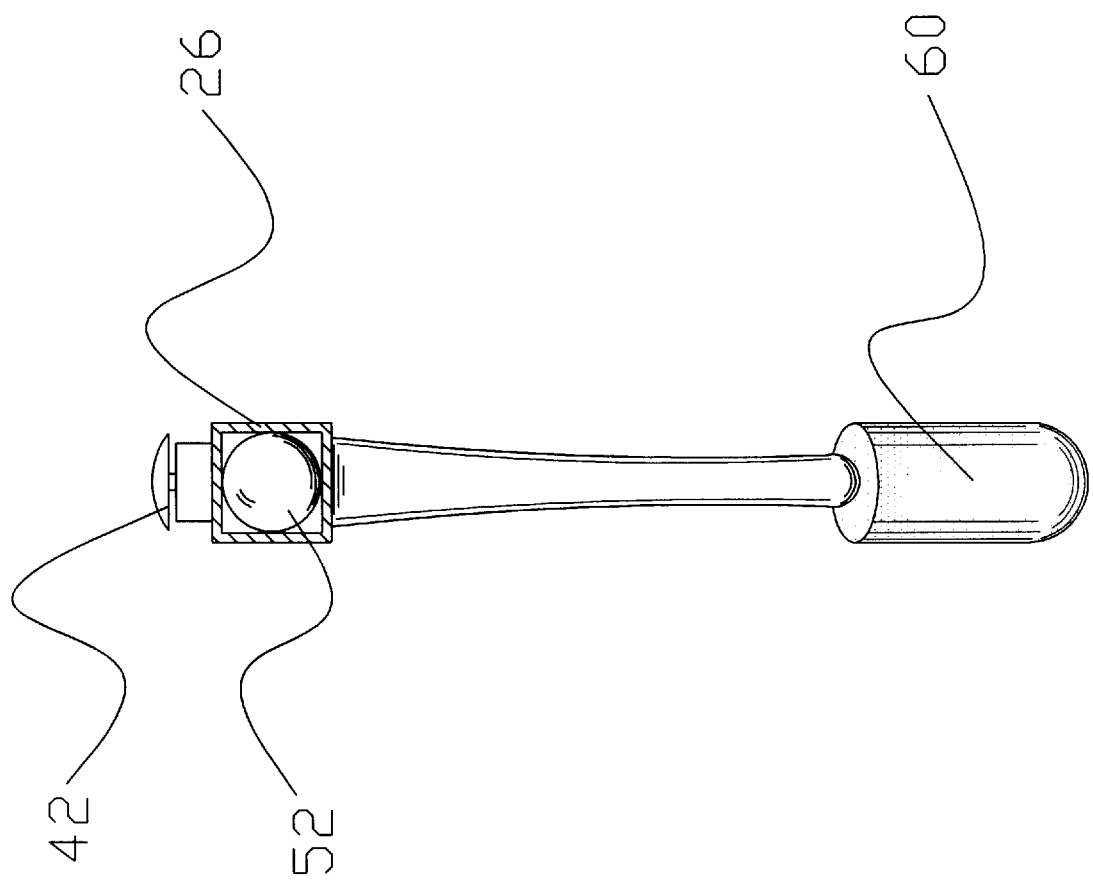
FIG. 10 is a cross sectional view taken along line 10—10 of FIG. 8.

An alternative embodiment of the present invention is illustrated in FIGS. 6 through 10 of the drawings. In the alternative embodiment of the present invention, the arms 26 of the glasses 20 are tubular in structure having an inner lumen 28 as best illustrated in FIGS. 8 through 10 of the drawings. A guide aperture 29 within the distal end of each of the arms 26 dispenses the cord 50 similar to the recoil device 40. A compression spring 70 is positioned within the lumen 28 of each of the arms 26 and is positioned adjacent a partition member 27 with an aperture within that allows the cord 50 to pass through. An engaging member 52 is positioned adjacent the end of the compression spring 70 opposite of the partition member 27 as best illustrated in FIG. 9 of the drawings. The engaging member 52 is attached to the length of cord 50 opposite of the earplug 60 as illustrated in FIGS. 8 and 9 of the drawings. As shown in FIGS. 6 through 10 of the drawings, the locking button 42 is positioned within the arms 26 of the glasses 20 to allow selective locking of the cord 50. FIG. 9 illustrates the locking button 42 depressed thereby retaining the engaging member 52 and compression spring 70 compressed thereby maintaining the cord 50 in a dispensed position with respect to the arms 26 of the glasses 20 through the respective guide aperture 29.

In use, the user positions opening of the connector 30 adjacent the distal end of one of the arms 26 of the glasses 20. The glasses 20 may be comprised of any conventional glasses 20 such as but not limited to prescription glasses 20, sunglasses 20 or safety glasses 20. The user then manipulates the connector 30 about the distal portion of the arm 26 until the connector 30 is snugly positioned about the arm 26. The same process is repeated for the opposing arm 26 of the glasses 20. The user then positions the glasses 20 upon their head as they normally would wear the glasses 20 without any interference from the earplugs 60. When the user desires to utilize the earplugs 60, the user simply grasps one earplug 60 and draws the cord 50 outwardly from the recoil device 40 which accordingly dispenses the cord 50 as shown in FIG. 2 of the drawings. Once the desired length of cord 50 is dispensed from the recoil device 40, the user then depresses the locking button 42 to prevent the recoil device 40 from drawing the cord 50 back into the recoil device 40. The user then positions the selected earplug 60 into their ear as desired. The same process is utilized to utilize the opposing earplug 60. When finished utilizing the earplugs 60, the user simply removes each earplug 60 releases the locking button 42 which allows each recoil device 40 to draw in the respective cord 50 along with the respective earplug 60 as shown in FIGS. 1 and 3 of the drawings. The same process is utilized with the alternative embodiment to dispense and store each earplug 60 except for the usage of the connector 30.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed to be within the expertise of those skilled in the art, and all equivalent structural variations and relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

We claim:

1. An earplug system for attaching to the distal end of an arm of glasses, comprising:
   a connector formed for attaching to the distal end of the arm of glasses;
   a recoil device attached to said connector;
   a length of cord stored within and dispensed from said recoil device; and
   an earplug attached to said cord.

2. The earplug system of claim 1, wherein said connector is comprised of a tubular structure.

3. The earplug system of claim 2, wherein said connector is comprised of a resilient material.

4. The earplug system of claim 3, wherein said connector is comprised of a rubber material.

5. The earplug system of claim 2, wherein said connector is comprised of a rigid material.

6. The earplug system of claim 1, including a hinge positioned between said connector and said recoil device for allowing said recoil device to pivot with respect to said connector.

7. The earplug system of claim 6, wherein said recoil device includes a locking button for allowing selecting locking of a position of said cord.

8. An earplug system, comprising:
   a pair of glasses having a frame, a first arm, and a second arm;
   a first recoil device attached to said first arm having a length of first cord stored within and dispensed from thereof; and
   a first earplug attached to said first cord.

9. The earplug system of claim 8, including a hinge positioned between said first arm and said first recoil device for allowing said first recoil device to pivot with respect to said first arm.

10. The earplug system of claim 8, wherein said first recoil device includes a first locking button for selecting the locking of a position of said first cord.

11. The earplug system of claim 8, including:
    a second recoil device attached to said second arm having a length of second cord stored within and dispensed from thereof; and
    a second earplug attached to said second cord.

12. The earplug system of claim 11, including a hinge positioned between said second arm and said second recoil device for allowing said second recoil device to pivot with respect to said second arm.

13. The earplug system of claim 12, wherein said second recoil device includes a second locking button for selecting the locking of a position of said second cord.

14. An earplug system, comprising:
    a frame having a first arm and a second arm, wherein said first arm has a tubular structure;
    a first compression spring positioned within said first arm;
    a length of first cord extending into said first arm through said compression spring and attached to an engaging member; and
    a first earplug attached to said first cord.

15. The earplug system of claim 14, including a locking button within said first arm for allowing selecting locking of a position of said first cord.

16. The earplug system of claim 14, wherein said second arm has a tubular structure and including:
    a second compression spring positioned within said second arm;
    a length of second cord extending into said second arm through said compression spring and attached to an engaging member; and
    a second earplug attached to said second cord.

17. The earplug system of claim 16, including a locking button within said second arm for allowing selecting locking of a position of said second cord.

18. The earplug system of claim 17, including a locking button within said first arm for allowing selecting locking of a position of said first cord.

* * * * *